US00PP18606P3

(12) United States Plant Patent
Larsen

(10) Patent No.: US PP18,606 P3
(45) Date of Patent: Mar. 18, 2008

(54) ***OSTEOSPERMUM* PLANT NAMED 'SUNNY DARK FLORENCE'**

(50) Latin Name: *Osteospermum ecklonis*
Varietal Denomination: Sunny Dark Florence

(75) Inventor: Bjarne N. Larsen, Odense (DK)

(73) Assignee: Amerinova Properties, LLC, Bonsall, CA (US)

( * ) Notice: Subject to any disclaimer, the term of this patent is extended or adjusted under 35 U.S.C. 154(b) by 27 days.

(21) Appl. No.: 11/387,164

(22) Filed: Mar. 23, 2006

(65) Prior Publication Data

US 2007/0226862 P1 Sep. 27, 2007

(51) Int. Cl.
*A01H 5/00* (2006.01)

(52) U.S. Cl. ..... Plt./360
(58) Field of Classification Search ..... Plt./360
See application file for complete search history.

(56) References Cited

PUBLICATIONS

GTITM UPOVROM Citation for 'Sunny Dark Florence' as per DK PBR 22113; Jul. 26, 2004.*

* cited by examiner

*Primary Examiner*—Kent Bell

(57) ABSTRACT

A new and distinct cultivar of *Osteospermum* plant named 'Sunny Dark Florence', characterized by its erect, compact growth habit, with short inflorescence stems, nonvariegated leaves, elliptic ray florets formed in one or two complete whorls, its vibrant orange ray floret color, with the under side of the ray florets having red-purple striations at the center and tips, and its dark violet-black disc florets.

1 Drawing Sheet

The present invention relates to a new and distinct cultivar of *Osteospermum* plant, botanically known as *Osteospermum ecklonis,* and referred to by the varietal denomination 'Sunny Dark Florence'.

The new cultivar is the product of a planned breeding program carried out by the inventor in Odense, Denmark. The objective of the breeding program was to create new *osteospermum* cultivars with distinctly new inflorescence colors.

The new cultivar was discovered and selected by the inventor in May 2004 as one naturally occurring flowering plant growing in a cultivated area in Odense, Denmark within a population of the parent cultivar 'Sunny Florence', the details of which are disclosed in U.S. Plant Pat. No. 17,307. The parent cultivar is characterized by its compact and upright but mounded plant habit, its dense and bushy growth habit, its freely flowering habit, and its cream or pale yellow colored ray florets and gray-colored disc florets. The ray florets of the new cultivar are a warmer, more vibrant orange in color, and the discs are darker.

The first act of asexual reproduction of the new cultivar was accomplished by terminal vegetative cuttings from the selection in April 2005 in a controlled environment in Odense, Denmark, by or under the supervision of the inventor. Horticultural examination of controlled flowerings of successive plantings has shown that the unique combination of characteristics of the new cultivar are firmly fixed and are retained through successive generations of asexual reproduction.

The new cultivar has not been observed under all possible environmental conditions. The phenotype may vary significantly with variations in environment, such as temperature, light intensity, and day length without, however, any variance in genotype.

SUMMARY OF THE INVENTION

The following traits have been repeatedly observed, and have been determined to be basic characteristics of the new cultivar, which in combination distinguish the new cultivar as being new and distinct:

1. The new cultivar has an erect, compact growth habit with short inflorescence stems.
2. Nonvariegated leaves.
3. Elliptic ray florets formed in one or two complete ray floret whorls.
4. The color of the top or upper surfaces of the ray florets is a vibrant orange (25B), and the under surfaces are the same background color but have red-purple stripes, mostly in the center and toward the tips. The disc florets are a nicely contrasting violet-black.

Of the many commercial cultivars known to the present inventor, the most similar cultivar in comparison to the new cultivar is the parent cultivar 'Sunny Florence'. The primary distinction is in ray and disc floret color, with the color of the upper side of the ray florets of 'Sunny Florence' being a very pale orange (RHS 28D), compared to the more vibrant orange ray floret color (25A for mature ray florets) for the new cultivar. The disc florets of the new cultivar are much darker.

BRIEF DESCRIPTION OF THE PHOTOGRAPHS

The first photograph shows a top perspective view of a pot containing two typical flowering plants of the new cultivar.

The second photograph is a view showing in greater detail the upper side of a mature inflorescence of the new cultivar.

The colors in the photographs show the colors as true as is reasonably possible with colored reproductions of this type. If any differences exist between the photographic color and the color values described below, the values in the detailed description are accurate.

DETAILED BOTANICAL DESCRIPTION

In the following description, color references are made to The Royal Horticultural Society Colour Chart. The values are based on plant material approximately 16 weeks old grown in Bonsall, Calif.

Botanical classification: *Osteospermum ecklonis* cv 'Sunny Dark Florence'.
Parentage: A spontaneous whole plant mutation of 'Sunny Florence'.
Propagation:
*Type.*—Terminal vegetative cuttings.
*Time to initiate roots.*—About 10 to 14 days at 18–21 degrees C.
*Root description.*—Fine, fibrous, and branching.
Disease/pest resistance or susceptibility: Good.
Temperature/Weather tolerance: Good tolerance to drought, rain, and wind, and temperatures down to about 0 degrees C.
Plant description:
*General appearance and shape.*—Generally oval and rangy.
*Habit.*—Generally upright with a loose, open habit; average vigor and branching.
*Plant height.*—36 cm.
*Plant diameter or area of spread.*—36 cm to 47 cm.
Lateral branching:
*Number or primary lateral branches.*—4.
*Number of secondary lateral branches.*—4–6.
*Length of primary branches.*—About 32 cm. to 36 cm.
*Diameter.*—About 0.4 cm. to 0.5 cm.
*Internode length.*—About 1.0 cm. to 1.5 cm.
*Texture.*—Smooth.
*Color.*—144B.
Foliage:
*Arrangement.*—Alternate.
*Simple or Compound.*—Simple.
*Length.*—About 3.5 cm. to 6.5 cm.
*Width.*—About 0.9 cm. to 1.5 cm; leaves become progressively smaller toward tip.
*Shape.*—Oblanceolate.
*Apex shape.*—Broadly acute.
*Base shape.*—Attenuate.
*Margin.*—Nearly entire but with irregular narrow projections.
*Texture.*—Smooth to glabrous.
*Color.*—Developing foliage: Upper surface 147A. Lower surface, 147A. Mature foliage: Upper surface, 147B. Lower surface, 147B.
*Venation, upper and lower surfaces.*—147B.
*Petiole length.*—About 1 cm.
*Petiole diameter.*—0.4 cm.
*Petiole color.*—Upper section, 147B; Lower section, 147B.
*Other foliage characteristics.*—Leaves have a dominant midvein and are irregularly reticulate.
Inflorescence:
*Appearance.*—Solitary, terminal, and axillary.
*Form.*—Single daisy; actinomorphic.
*Orientation.*—Terminals are upright, and axillary are inclined outwardly.
*Longevity.*—2–3 days.
*Fragrance.*—None.
*Quantity.*—1–8 open inflorescences on main stem and about 12 visible buds.
*Size.*—Total diameter: 7.0 cm.
*Depth.*—About 2.5 cm.
*Diameter of disc.*—1.3 cm.
*Receptacle diameter.*—About 2.5 cm.
*Receptacle height.*—1.4 cm.
*Buds (just before anthesis).*—Height: 2.3 cm. Diameter: 1.5 cm. Shape: Ovoid. Color: 24C.
Ray florets:
*Quantity per inflorescence.*—28.
*Shape.*—Elliptic
*Length.*—3.8 cm.
*Width.*—0.8 cm.
*Apex.*—Nearly round to minutely tridentate.
*Base.*—Acute.
*Margin.*—Entire.
*Texture.*—Smooth, satiny.
*Aspect.*—Most are about 60 deg. from vertical; not flat.
*Color.*—When opening: Upper surface 26B; Lower surface, 24C.
*Mature.*—Upper surface, 25A; Lower surface, 28C; With striations between 70B and 70C in center and tips.
Disc florets:
*Quantity per flower.*—Approximately 106.
*Shape.*—Tubular.
*Apex.*—Acute, with 5 points.
*Base.*—Fused at base into short tube.
*Length.*—0.8 cm.
*Width.*—At apex, 0.2 cm; At base, 0.1 cm.
*Color.*—Immature, 79A; Mature, between 79B and 79C. The violet-black discs contrast nicely with the vivid orange ray florets.
Involucral bracts:
*Quantity per flower.*—26.
*Length.*—1.5 cm.
*Width.*—0.25 cm.
*Shape.*—Lanceolate.
*Apex.*—Acute.
*Base.*—Truncate.
*Color.*—Upper surface, 146A; Lower surface, 147A.
Peduncles:
*Strength.*—Good.
*Aspect.*—Upright to outwardly angled at about 30–40 degrees.
*Length.*—Terminal peduncle about 7.5 cm., Third peduncle about 6.8 cm.
*Diameter.*—About 0.2 cm.
*Texture.*—Minutely pubescent.
*Color.*—45A.
Reproductive organs:
*Androecium.*—Stamens in disc florets.
*Stamen number.*—5.
*Anther shape and length.*—Oblong, about 0.3 cm.
*Anther color.*—Darker than 79A.
*Pollen color.*—23A.
*Gynoecium.*—On ray florets only.
*Pistil length.*—0.5 cm.
*Stigma shape.*—Bipartite; stigma color 79A.
*Style length.*—0.3 cm; style color 155A.
Seed/fruit: None observed.
Other inflorescence characteristics: Inflorescences close at night. The ray florets are very soft and delicate and tend to curl backward at tips, and curl under along margins with age. The ray floret color is a very attractive sort of marigold-orange, and the contrasting red-purple center stripe on the under surface is striking. The discs are dark and relatively small but develop an interesting ring effect as the anthers dehisce, revealing bright orange pollen. This produces a decorative, bulls-eye effect when viewed from above, somewhat similar to a black-eyed-Susan look, but one that does not fade.

I claim:

1. A new and distinct cultivar of *Osteospermum* plant named 'Sunny Dark Florence', as illustrated and described.

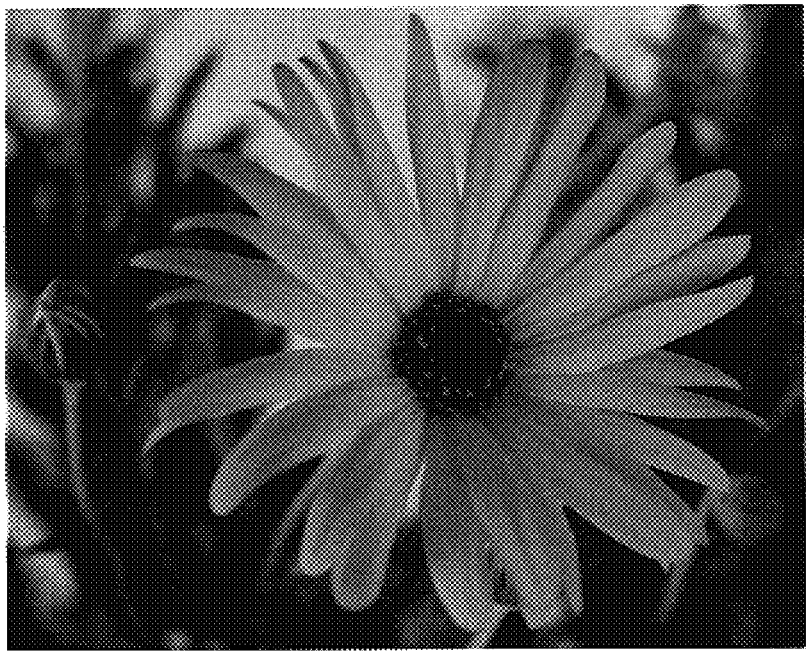
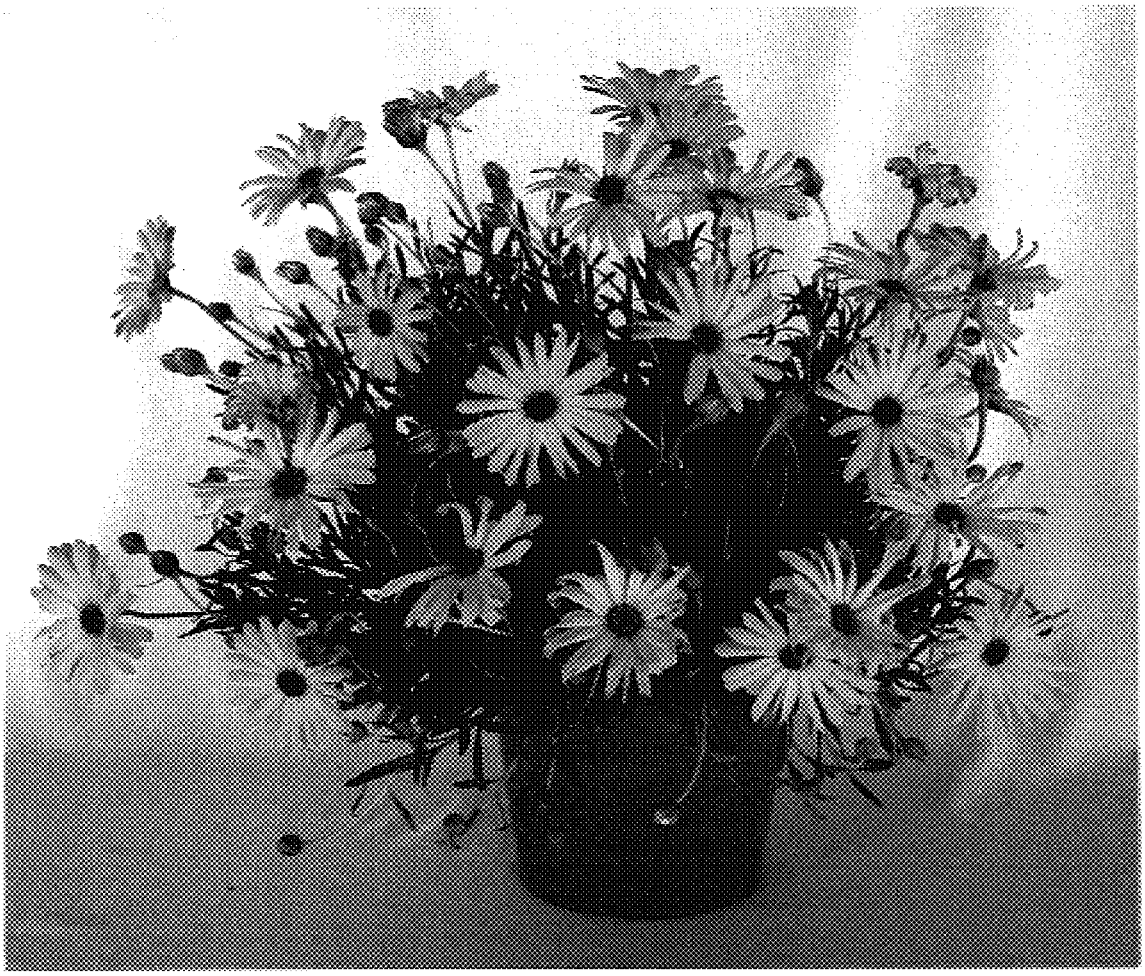

* * * * *